United States Patent
Kollar (10) Patent No.: US 9,889,109 B2
(45) Date of Patent: Feb. 13, 2018

(54) PHARMACEUTICAL COMPOSITION COMPRISING BENZYL ALCOHOL FOR THE TREATMENT OF MIGRAINES

(71) Applicant: St. Renatus, LLC, Fort Collins, CO (US)

(72) Inventor: Mark D. Kollar, Fort Collins, CO (US)

(73) Assignee: ST. RENATUS, LLC, Fort Collins, CO (US)

(*) Notice: Subject to any disclaimer, the term of this patent is extended or adjusted under 35 U.S.C. 154(b) by 0 days.

(21) Appl. No.: 14/431,904

(22) PCT Filed: Sep. 27, 2013

(86) PCT No.: PCT/US2013/062353
§ 371 (c)(1),
(2) Date: Mar. 27, 2015

(87) PCT Pub. No.: WO2014/052859
PCT Pub. Date: Apr. 3, 2014

(65) Prior Publication Data
US 2015/0246017 A1    Sep. 3, 2015

Related U.S. Application Data

(60) Provisional application No. 61/707,420, filed on Sep. 28, 2012.

(51) Int. Cl.
A61K 31/245 (2006.01)
A61K 31/045 (2006.01)
A61K 9/16 (2006.01)
A61K 9/08 (2006.01)
A61K 9/00 (2006.01)

(52) U.S. Cl.
CPC .......... A61K 31/245 (2013.01); A61K 9/0043 (2013.01); A61K 9/16 (2013.01); A61K 31/045 (2013.01); A61K 9/08 (2013.01)

(58) Field of Classification Search
None
See application file for complete search history.

(56) References Cited

U.S. PATENT DOCUMENTS

| | | | |
|---|---|---|---|
| 4,559,328 A | 12/1985 | Smerbeck | |
| 5,840,755 A | 11/1998 | Levin | |
| 5,939,425 A | 8/1999 | Caruso | |
| 6,432,986 B2 | 8/2002 | Levin | |
| 6,491,940 B1 | 12/2002 | Levin | |
| 7,273,887 B1 | 9/2007 | Wepfer | |
| 7,799,337 B2 | 9/2010 | Levin | |
| 2001/0055607 A1 | 12/2001 | Levin | |
| 2002/0010194 A1 | 1/2002 | Levin | |
| 2003/0013387 A1 | 1/2003 | Tsai | |
| 2004/0142944 A1* | 7/2004 | Serno | A61K 9/0043 514/262.1 |
| 2004/0219229 A1 | 11/2004 | Clarot | |
| 2004/0229920 A1 | 11/2004 | Garvey | |
| 2010/0030187 A1 | 2/2010 | Xia | |
| 2010/0030188 A1 | 2/2010 | Tian | |
| 2010/0137940 A1 | 6/2010 | Levin | |
| 2011/0008408 A1 | 1/2011 | Shalev | |
| 2011/0118189 A1 | 5/2011 | Farr | |
| 2012/0039960 A1 | 2/2012 | Kollar | |
| 2012/0065259 A1 | 3/2012 | Zhang | |

FOREIGN PATENT DOCUMENTS

| | | |
|---|---|---|
| CA | 2297097 | 4/2007 |
| EP | 999839 | 7/1998 |
| WO | WO-1999003473 | 1/1999 |
| WO | WO-2000004432 | 1/2000 |
| WO | WO-2009134336 | 11/2009 |

OTHER PUBLICATIONS

Barre, "Cocaine as an abortive agent in cluster headache," Headache, 22(2):69-73 (1982).
Generali, "Intranasal Lidocaine: Migraine Headaches," Hospital Pharmacy, 36(2):192-196 (2001).
Guay, "Methemoglobinemia related to local anesthetics: a summary of 242 episodes," Anesthesia & Analgesia, 108(3):837-845 (2009).
Johnson et al., "Trigeminal pathways deliver a low molecular weight drug from the nose to the brain and orofacial structures," Molecular Pharmaceutics, 7(3):884-893 (2010).
Kalso et al., "Systemic local-anaesthetic-type drugs in chronic pain: a systematic review," European Journal of Pain, 2(1):3-14(1998).
Kudrow et al., "Rapid and sustained relief of migraine attacks with intranasal lidocaine: preliminary findings," Headache, 35(2):79-82 (1995).
Lidocaine, Medication, www.headaches.org/education/medications/lidocaine (downloaded Aug. 22, 2012) (1 page).
Maizels et al., "Intranasal lidocaine for migraine: a randomized trial and open-label follow-up," Headache, 39(8):543-551 (1999).
Marin et al., "Efficacy of tetracaine intranasal vs. oral acute attack of migraine eletriptan," Neurologia, Neurocirugia Y Psiquiatria 2011 Sociedad Mexicana De Neurologia Y Psiquiatria Mex, 44(3):81-87 (2011) (EMB-2011579090) (1 page).
Onizuka et al., "Local Anesthetics with High Lipophilicity are Toxic, While Local Anesthetics with Low pka Induce More Apoptosis in Human Leukemia Cells," Journal of Anesthesia & Clinical Research, 2(116):1-5 (2011).

(Continued)

Primary Examiner — David J Blanchard
Assistant Examiner — Sarah Chickos
(74) Attorney, Agent, or Firm — Foley & Lardner LLP; Karen Mangasarian; Gitanjali Chimalakonda (57) ABSTRACT

The present invention relates to intranasally administered pharmaceutical compositions for the treatment of headaches, such as migraines. Such pharmaceutical compositions comprise benzyl alcohol or a combination of benzyl alcohol and tetracaine. The invention also relates to methods for treating headaches, such as migraines, using these pharmaceutical compositions.

13 Claims, 3 Drawing Sheets (56) References Cited

OTHER PUBLICATIONS

Ramos-Reyna et al., Estudio clinico aleatorizado de tetracaina intranasal versus placebo en el ataque agudo de migraña en el Hospital Central Militar, Neuroscience Archives, 13(4):237-241 (2008).
Reutens et al., "Is intravenous lidocaine clinically effective in acute migraine?," Cephalalgia, 11(6):245-247 (1991).

* cited by examiner

PHARMACEUTICAL COMPOSITION COMPRISING BENZYL ALCOHOL FOR THE TREATMENT OF MIGRAINES

REFERENCE TO RELATED APPLICATIONS

This application is a national stage filing under 35 U.S.C. 371 of International Application PCT/US2013/062353 filed Sep. 27, 2013, which claims the benefit of U.S. Provisional Patent Application 61/707,420 filed Sep. 28, 2012, the specifications of which are incorporated by reference herein. International Application PCT/US2013/062353 was published under PCT Article 21(2) in English.

TECHNICAL FIELD OF INVENTION

The present invention relates to intranasally administered pharmaceutical compositions for the treatment of headaches, such as migraines. Such pharmaceutical compositions comprise benzyl alcohol or a combination of benzyl alcohol and tetracaine. The invention also relates to methods for treating headaches, such as migraines, using these pharmaceutical compositions.

BACKGROUND OF THE INVENTION

Headaches are a common condition affecting millions of people in the United States alone. Headaches are generally classified into two categories: primary and secondary headaches. Primary headaches are those which are not associated with or caused by other diseases. They include migraines, tension-type headaches, cluster headaches, and other headaches such as stabbing, cough, exertional, hypnic, and thunderclap headaches. In contrast, secondary headaches are caused by an underlying structural problem in the head or neck. Secondary headaches include those attributed to head and/or neck trauma, cranial and/or cervical vascular disorders, non-vascular intracranial disorders, substance use, withdrawal from substance use, infection, physical disorders or psychiatric disorders.

Migraines are a chronic disorder characterized by recurring moderate to severe headaches. The World Health Organization has noted the disabling effect of migraines and reports that migraines are $19^{th}$ among all causes of years lived with disability. In addition to headache pain, migraines are also associated with nausea, vomiting, photophobia, phonophobia, disturbances in taste, and disturbances in hearing. Migraines are typically unilateral and pulsating in nature and may last anywhere from between several hours to 3 days. Up to one-third migraine sufferers perceive an aura which can manifest itself as a transient visual, sensory, language, or motor disturbance. Such auras typically signal that a migraine will soon occur.

Because the causes of primary headaches (e.g., migraines) are highly varied and often unknown, treatment methods have been met with a lack of consistency and efficacy. For example, current migraine treatments can be characterized as abortive (i.e., treatments to abort current migraines) or preventative (i.e., treatments to prevent future migraines). Abortive treatments can be administered orally, nasally, or by injection. Triptans, such as IMITREX®, which specifically target serotonin, are commonly used as abortive migraine treatments. Examples of drugs used for abortive treatments include almotriptan, eletriptan, frovatriptan, naratriptan, rizatriptan, sumatriptan, zolmitriptan, acetaminophen-isometheptene-dichloralphenazone, dihydroergotamine, ergotamine tartrate, ibuprofen, and aspirin-acetaminophen-caffeine. Preventative treatments are typically considered if migraines occur frequently (e.g., more than once per week) or if migraine symptoms are severe. Preventive treatments include beta-blockers (e.g., propranolol, timolol), calcium channel blockers (e.g., verapamil), antidepressants (e.g., amitriptyline, nortriptyline), antiseizure medications (e.g., gabapentin, topiramate, valproic acid), and BOTOX®. However, such treatments may be accompanied by unpleasant side effects. For example, side effects associated with verapamil include constipation, dizziness, nausea, fatigue, swelling of the ankles and low blood pressure. Side effects associated with IMITREX® include anxiety, burning, numbness or tingling of the skin, dizziness, drowsiness, muscle aches or cramps, nausea, neck stiffness, upset stomach, throat or sinus discomfort, tingling, tiredness, vomiting, and weakness.

Current cluster headache treatments have also met with varying success. Abortive treatments include oxygen, triptans, octreotide (e.g., sandostatin), local anesthtics (e.g., lidocaine), and dihydroergotamine. Though some treatments are more effective than others, treatments such as intranasal administration of lidocaine are not consistently effective in aborting cluster headache pain. Some preventative options are also available including calcium channel blockers, corticosteroids, lithium (e.g., Lithobid), nerve blocks (e.g., injecting an anesthetic and corticosteroid into the area around the occipital nerve), ergots (e.g., Ergomar), and melatonin. Again, such treatments are accompanied by unpleasant side effects including those typically associated with corticosteroids (e.g., corticosteroid withdrawal syndrome, hyperglycemia, insulin resistance, diabetes mellitus, osteoporosis, cataract, anxiety, depression, colitis, hypertension, ictus, erectile dysfunction, hypogonadism, hypothyroidism, amenorrhoea, and retinopathy), lithium (e.g., tremors, increased urination, diarrhea, and possible kidney damage), and verapamil (as described above).

Intravenous administration of lidocaine has been shown to demonstrate a limited benefit over placebo in the treatment of acute migraines, but has failed to demonstrate clinically significant efficacy (Reutens, et al., Cephalalgia, 11(6):245-247, 1991). Intranasal administration of local anesthetics, such as lidocaine, for the relief of migraine pain has also been explored as a treatment option. However, studies investigating lidocaine treatment indicate that there can be a low rate of efficacy (Kudrow et al., Headache, 35:79-82, 1995), or that patients experience relapses of pain soon after treatment and/or suffer from pronounced local adverse events (Maizels et al., J. Amer. Med. Assoc. 276:319-321, 1996). In addition, lidocaine has been associated with serious side-effects such as methemoglobinemia (Guay, Anesth Analg., 108(3):837-45, 2009) and toxic metabolic byproducts such as 2,6-xylidine and 4-hydroxyxylidine (as is common for amide-based anesthetics). Treatment with other local anesthetics have also met with disappointing results.

Other procedures have been recommended to decrease the frequency of headaches. In the context of migraines, such procedures include surgery, counseling, and participation in biofeedback procedures. In the context of cluster headaches, such procedures include surgery, implantation of devices to stimulate the occipital nerve, and implantation of stimulators in the hypothalamus. However, the efficacy of these treatments is debated and some, such as surgery, carry the risk of serious side effects.

Because the currently available treatments for headaches suffer from varying degree of effectiveness, length of efficacy, and/or lack of consistency of efficacy, there remains a need for effective and safe headache treatments which preferably provide increased length of efficacy.

SUMMARY OF THE INVENTION

The present invention provides an intranasally administered, benzyl alcohol-based composition which is useful for treating headaches.

The pharmaceutical composition is typically administered to specific tissues such as the lymphoepithelial tissues. In some embodiments, the pharmaceutical composition is administered to at least parts of the nasopharynx, the superior soft palate, and/or the tonsillar area. In other embodiments, the pharmaceutical composition is administered to the Waldeyer's tonsillar ring and/or the fossa of Rosenmuller.

In one aspect, the invention provides a pharmaceutical composition for intranasal administration comprising: a) benzyl alcohol; and b) a pharmaceutically acceptable carrier. In some embodiments, the composition comprises about 0.6-1.2% (w/v) benzyl alcohol. In other embodiments, the composition comprises about 0.75-1.05% (w/v) benzyl alcohol. In one embodiment, the composition comprises about 0.9% (w/v) benzyl alcohol.

In another aspect, the invention provides a pharmaceutical composition for intranasal administration comprising: a) benzyl alcohol; b) tetracaine, or a pharmaceutically acceptable salt thereof; and c) a pharmaceutically acceptable carrier. In some embodiments, the composition comprises about 0.6-1.2% (w/v) benzyl alcohol. In other embodiments, the composition comprises about 0.75-1.05% (w/v) benzyl alcohol. In one embodiment, the composition comprises about 0.9% (w/v) benzyl alcohol. In some embodiments, the composition comprises about 2-4% (w/v) tetracaine. In some embodiments, the composition comprises about 2.5-3.5% (w/v) tetracaine. In other embodiments, the composition comprises about 3% (w/v) tetracaine. In a particular embodiment, the composition comprises 0.9% (w/v) benzyl alcohol and 3% (w/v) tetracaine.

In some embodiments, the intranasal pharmaceutical composition further comprises a preservative (i.e., in addition to benzyl alcohol which is itself a preservative). Examples of preservatives include, but are not limited to sugar alcohols (e.g., sorbitol and mannitol), chlorobutanol, benzalkonium chloride, alcohols (e.g., ethanol, isopropanol, chlorobutanol, cresol, chlorocresol, and phenol) and benzalkonium chloride (BAK).

In some embodiments, the intranasal pharmaceutical composition further comprises a viscosity enhancing agent. In some embodiments, the viscosity enhancing agent includes, but is not limited to methylcellulose, hydroxyethylcellulose, hydroxypropylmethylcellulose and smart hydrogel. In some embodiments, the viscosity enhancing agent is hydroxyethylcellulose. In some embodiments, the intranasal pharmaceutical composition comprises about 0.01-1.0% (w/v) hydroxyethylcellulose. In other embodiments, the intranasal pharmaceutical composition comprises about 0.05% (w/v) hydroxyethylcellulose.

In some embodiments, the intranasal pharmaceutical composition is formulated as a gel or a liquid. In some embodiments the liquid is water, a sugar alcohol, an alcohol (e.g., ethanol), or any other solvent that is biologically compatible with the target tissue.

In some embodiments, the pH of the intranasal pharmaceutical composition is between about 4.0 to about 7.5. In other embodiments, the pH of the pharmaceutical composition is between about 4.0 to about 6.5. In another embodiment the pharmaceutical composition has a pH of about 5.5 to about 6.5. In further embodiments, the pharmaceutical composition has a pH of about 6.0 to about 6.5.

In one embodiment, the intranasal pharmaceutical composition comprises benzyl alcohol. In another embodiment, the intranasal pharmaceutical composition comprises benzyl alcohol and tetracaine. In yet another embodiment, the intranasal pharmaceutical composition comprises benzyl alcohol, tetracaine HCl, anhydrous citric acid (for pH control), sodium hydroxide (for pH adjustment), hydrochloric acid (for pH control), hydroxyethylcellulose, and purified water.

In a particular embodiment, the intranasal pharmaceutical composition of the present invention comprises the components, and respective amounts, listed in Table 1 below (referred to herein as the "Table 1 Pharmaceutical Composition.")

TABLE 1

| Ingredient | Pharmaceutical Composition (% w/v) |
|---|---|
| Benzyl alcohol, NF | 0.90 |
| Citric acid anhydrous, USP | 1.00 |
| Sodium hydroxide, NF | q.s. |
| Hydrochloric acid, NF | q.s. |
| Hydroxyethylcellulose, NF (5000 cps) | 0.05 |
| Purified water, USP | q.s. to 100% |

In another particular embodiment, the intranasal pharmaceutical composition of the present invention comprises the components, and respective amounts, listed in Table 2 below (referred to herein as the "Table 2 Pharmaceutical Composition.")

TABLE 2

| Ingredient | Pharmaceutical Composition (% w/v) |
|---|---|
| Benzyl alcohol, NF | 0.90 |
| Tetracaine hydrochloride, USP | 3.00 |
| Citric acid anhydrous, USP | 1.00 |
| Sodium hydroxide, NF | q.s. |
| Hydrochloric acid, NF | q.s. |
| Hydroxyethylcellulose, NF (5000 cps) | 0.05 |
| Purified water, USP | q.s. to 100% |

In another aspect, the invention provides a method for treating a headache by intranasally administering the compositions described herein. The method comprises selectively delivering to the nasopharynx and tonsillar tissues of the subject a pharmaceutical composition of the invention, wherein at least a portion of the pharmaceutical composition is absorbed by nasal tissue located near the Waldeyer's tonsillar ring and/or fossa of Rosenmuller, thereby relieving the subject of at least part of the pain associated with the headache. In one embodiment, the headache is a migraine. In some embodiments the subject is relieved of all of the pain associated with the headache. In some embodiments, the pharmaceutical composition is delivered by spraying. In other embodiments, the delivered spray is a stream or a plume.

In some embodiments, the particle size of the pharmaceutical composition delivered to the rear of the nasal cavity is about 5-50 microns. In other embodiments, the particle size of the pharmaceutical composition is about 10-20 microns. In other embodiments, the pharmaceutical composition is delivered in a manner such that at least 85% of the particles are at least about 10 microns or larger. In yet other embodiments, the particle size of the pharmaceutical composition is about 10 microns or larger.

In another aspect, the invention provides a spray device for intranasal delivery of a pharmaceutical composition of the present invention. In some embodiments, the spray device is capable of delivering the intranasal pharmaceutical composition to the nasal tissue located at the rear of the nasal cavity. In other embodiments, the spray device is capable of delivering the intranasal pharmaceutical composition to the nasal tissue located at the rear of the nasal cavity in the vicinity of the nasopharynx and tonsillar tissues including, e.g., the Waldeyer's tonsillar ring and/or fossa of Rosenmuller. In yet other embodiments, the spray device is pre-filled with an intranasal pharmaceutical composition of the present invention.

In some embodiments, the method comprises spraying the intranasal pharmaceutical composition of the invention 1-5 times into each of the nostrils of the subject. In other embodiments, the method comprises spraying the pharmaceutical composition of the invention 3 times into each of the nostrils of the subject. In other embodiments, the method comprises spraying the pharmaceutical composition of the invention 2 times into each of the nostrils of the subject. In other embodiments, the method comprises spraying the pharmaceutical composition of the invention 1 time into each of the nostrils of the subject. In yet other embodiments, the method comprises spraying the pharmaceutical composition of the invention 1 time into the nostril located on the same side of the head as the predominant headache pain. In some embodiments, each of the sprays are administered within about 1-10 minutes, of each other. For example, spray #1 may be administered, followed by an interval of about 1-10 minutes, after which spray #2 is administered, followed by an interval of about 1-10 minutes, after which spray #3 is administered, etc. In some embodiments, the interval between sprays is about 2-6 minutes. In other embodiments, the interval between sprays is about 3-5 minutes. In yet other embodiments, the interval between sprays is about 4 minutes.

When treated with the composition of the present invention in accordance with the methods described herein, in some embodiments, the subject experiences a reduction in pain associated with the headache within 1-30, 1-25, or 1-20 minutes of treatment. In some embodiments, the subject will experience a reduction in pain associated with the headache within 1-15 or 1-10 minutes of treatment. In some embodiments, the subject will experience a reduction in pain associated with the headache within 1, 2, 3, 4, 5, 6, 7, 8, 9, 10, 11, 12, 13, 14, or 15 minutes of treatment. In some embodiments, the subject will experience a reduction in pain associated with the headache within 1, 2, 3, 4 or 5 minutes of treatment. In one embodiment, the headache is a migraine.

When treated with the composition of the present invention in accordance with the methods described herein, in some embodiments, the subject experiences a partial reduction in pain associated with the headache. In other embodiments, the subject experiences at least a 5, 10, 15, 20, 25, 30, 35, 40, 45, 50, 55, 60, 65, 70, 75, 80, 85, 90, or 95% reduction in pain associated with the headache. In other embodiments, the subject experiences a 25, 50, or 75% reduction in pain associated with the headache.

In some embodiments, the subject experiences a complete reduction in pain associated with the headache. In some embodiments, the headache pain does not return for a period of 2-72, 2-60, 2-48, 2-36, 2-24, 2-12, 2-10, 2-8, 2-6, or 2-4 hours. In other embodiments, the headache pain does not return for 2, 3, 4, 5, 6, 7, 8, 9, 10, 11, 12, 13, 14, 15, 16, 17, 18, 19, 20, 21, 22, 23, 24, 30, 36, 42, 48, 54, 60, 66, or 72 hours. In some embodiments, the headache pain does not return for 1, 2, 3, 4, 5, 6, 7, 8, 9, 10, 11, 12, 13, or 14 days. In some embodiments, the headache pain does not return for 1, 2, 3, or 4 weeks. In some embodiments, the headache pain does not return for more than 1, 2, 3 or 4 weeks. In one embodiment, the headache is a migraine.

BRIEF DESCRIPTION OF THE FIGURES

FIG. 1 is a cross-sectional side view of a human nasal cavity, and associated nerves and relevant anatomical structures. Both the greater and lesser palatine nerves originate at the pterygopalatine (sphenopalatine) ganglion (SPG). The anterior, middle and posterior superior alveolar nerves originate at the maxillary nerve. The nasopalatine branch of the anterior superior alveolar nerve communicates between the alveolar nerves and the palatine nerves. The $2^{nd}$ cranial nerve (ophthalmic nerve) is the nerve that connects the eye to the brain and carries the impulses formed by the retina. The $3^{rd}$ cranial (oculomotor) nerve is one of the cranial nerves that control eye movement and divides into the nasociliary branch. The trigeminal nerve, also known as the $5^{th}$ cranial nerve, is responsible for the production of much of the external and internal sensations of pain, temperature and touch to the head and face, including head pain (e.g., headache, such as a migraine). The trigeminal nerve has three major branches—the ophthalmic nerve, which carries sensation from the eye area and forehead; the maxillary nerve, which carries sensation from the middle part of the face; and the mandibular nerve, which carries sensation from the lower part of the mouth and the jaw. The $7^{th}$ cranial nerve (facial nerve), as well as the secondary branches, i.e., auriculotemporal nerve (branch of the mandibular nerve), transmit pain impulses from the soft palate to the brain. Additional cranial nerves in the localized region are the $9^{th}$ and $10^{th}$ cranial nerves (glossopharangeal and vagus respectively).

As shown in FIG. 2, the trigeminal nerve has three divisions which enervate the forehead, eye (ophthalmic V1), cheek (maxillary V2) and lower face and jaw (mandibular V3). The trigeminal nerves function in sensing facial touch, pain and temperature, as well as controlling muscles used for chewing. The three divisions of the trigeminal nerve shown come together in an area called the Gasserion ganglion. At that point, the trigeminal nerve root continues back towards the side of the brain stem, and inserts into the pons. Within the brain stem, the signals traveling through the trigeminal nerve reach specialized clusters of neurons called the trigeminal nerve nucleus. Because the trigeminal nerve structures are integral and commonly associated with headaches, the disclosed pharmaceutical compositions appear to have far reaching effects to these deep structures as well as the midbrain.

FIG. 3 illustrates the intranasal delivery of a pharmaceutical composition for medical treatment of migraines and headaches. The nasal cavities, concha, sinuses and nasopharynx are depicted. An amount of the pharmaceutical composition of the present invention is dispensed into the nostril, thereby delivering the pharmaceutical composition topically throughout the region, and affecting the neural structures involved in migraine symptoms. Generally, specific anatomical targeting of the compound is not necessary. Because the pharmaceutical composition has been designed for maximum penetration, uptake and infusion, a wide range of neural structures are subject to the pain-mitigating effects. This provides a system and method that is versatile, easy to administer and has widespread applications for headaches triggered by a wide variety of mechanisms.

DETAILED DESCRIPTION OF THE INVENTION

In order that the invention herein described may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

In order to further define the invention, the following terms and definitions are provided herein.

Definitions

"Anesthetic" as used herein is a compound or agent that prevents or reduces sensation and/or pain.

"Anesthetizing" as used herein refers to administering an anesthetic compound for the purpose of preventing or reducing sensation and/or pain.

"Benzyl alcohol" as used herein refers to the organic compound with the formula $C_6H_5CH_2OH$. Benzyl alcohol is also referred to as "phenylmethanol," "phenol carbinol," "phenylcarbinol," "benzenemethanol," "alpha-hydroxytoluene," "phenyl carbinol," and "phenylmethyl alcohol."

"Headache" (also referred to as "cephalalgia," "cephalea," or "cephalgia") as used herein refers to pain in the head which can either arise from many disorders, or can be a disorder in and of itself. Headaches are divided into two categories: primary and secondary. Primary headaches (i.e., those not associated with or caused by other diseases) include migraines (vascular headaches), tension-type headaches (muscular contraction headache), cluster headaches, and other headaches such as stabbing, cough, exertional, hypnic, and thunderclap headaches. Secondary headaches (i.e., those caused by an underlying structural problem in the head or neck), include those attributed to head and/or neck trauma, cranial and/or cervical vascular disorders, non-vascular intracranial disorders, substance or its withdrawal, infection, physical disorders or psychiatric disorders. The pharmaceutical compositions of the present invention are useful in treating both primary and secondary headaches. One of skill in the art would understand that, depending on how headaches are classified, one can identify dozens of types of headaches. All types of headaches, however, are envisioned in the context of the present invention.

"Local anesthetic" as used herein refers to an anesthetic delivered near the nerve ending to be anesthetized which diffuses after introduction inside the tissue. A local anesthetic is capable of penetrating the tissue deep enough so as to reach the target nerves. A local anesthetic is different from a "topical anesthetic" in that a topical anesthetic only provides surface anesthesia to a depth of approximately 1-2 mm. A topical anesthetic does not penetrate deep enough in the tissue to reach nerves.

"Migraine" as used herein refers to headaches which may be accompanied by symptoms including nausea, vomiting, or sensitivity to light. The pain associated with migraines is typically described as a unilateral throbbing pain. Migraines may be preceded by visual disturbances such as aura, flashing lights, wavy lines, strange taste or odor, numbness, tingling, vertigo, tinnitus, or a feeling that part of the body is distorted in size or shape.

"Preceding nerves" as used herein refers to nerves located upstream, usually present in a more central neural bundle, from a particular reference nerve.

"Subject" as used herein refers to an animal including a mammal (e.g., a human).

"Tetracaine" (sometimes referred to as "amethocaine") as used herein refers to (2-(dimethylamino)ethyl 4-(butylamino)benzoate) and any salt thereof. Tetracaine HCl refers to the HCl salt of 2-(dimethylamino)ethyl 4-(butylamino) benzoate.

"(% w/v)" refers to % weight/volume. Any units may be used in connection with this term. However, unless otherwise specified, the notation "(% w/v)" refers to a % of a composition where w/v refers to grams/100 milliliters.

Pharmaceutical Compositions

In one aspect, the present invention relates to pharmaceutical compositions for the treatment of headaches, such as migraines. The pharmaceutical compositions of the present invention offer the advantage over conventional treatments by providing a novel and effective treatment that is rapid, narcotic-free and injection-free.

The present invention is based upon the discovery that nasal administration of benzyl alcohol has been found to reduce the pain due to a headache in a subject. The headaches may be either primary or secondary headaches. In some embodiments, the headache is a primary headache such as a migraine, tension-type headache, cluster headache, or other headache (e.g., stabbing, cough, exertional, hypnic, or thunderclap headache). In some embodiments, the headache is a secondary headache such as one attributed to head and/or neck trauma, cranial and/or cervical vascular disorders, non-vascular intracranial disorders, substance use, withdrawal from substance use, infection, physical disorders or psychiatric disorders. In one embodiment, the headache is a migraine.

Without being bound by a particular theory, it is believed that benzyl alcohol mitigates pain by acting on one or more of the $1^{st}$, $3^{rd}$, $5^{th}$, $7^{th}$, $9^{th}$, $10^{th}$, and $12^{th}$ cranial nerves upon administration into the nasal cavity, thereby providing pain relief from the headache. Such a discovery is surprising in light of the fact that benzyl alcohol—a common component of fragrances, air fresheners, and perfumes—is known to induce headaches (see, e.g., International Chemical Safety Card (ICSC) regarding benzyl alcohol). Moreover, the fact that benzyl alcohol acts to reduce pain associated with headaches at the low concentrations present in, e.g., the Table 1 Pharmaceutical Composition, is surprising. For example, in the context of intranasally administered drugs, the FDA considers benzyl alcohol to be an "active ingredient" at concentrations of 1% and above and a preservative at concentrations below 1%.

Benzyl alcohol may also reduce pain due to headaches via other pathways. For example, benzyl alcohol is known to degrade substance P, an inflammatory chemical which causes vasodilation and inflammation and, in turn, causes activation of the spinal trigeminal nucleus which processes pain. Degradation of substance P may lead to reduced activation of the spinal trigeminal nucleus. Along those lines, at some concentrations, benzyl alcohol inhibits acetylcholinesterase (AchE), which is responsible for the release of neurotransmitter pain mediators including substance P. Inhibition of AchE by benzyl alcohol inhibition may act to modify, e.g., sodium and/or calcium channels thus blocking migraine pain.

Previous studies have explored the use of nasally administered anesthetics such as cocaine and lidocaine for the treatment of headache pain. Although cocaine—an addictive compound which is not suitable in most settings—was found to relieve pain due to a single cluster headache episode (i.e., a headache with short duration), its effect was found to be short-lived (Barre, *Headache*, 22:69-73 (1982)). Moreover, repeat administrations of cocaine were necessary. Such results are in line with the relatively short duration of anesthetic effect observed with cocaine. Studies involving the use of intranasal lidocaine, which also exhibits a relatively short anesthetic effect, demonstrated that although lidocaine was able to reduce pain associated with headaches in some circumstances, low rates of efficacy, relapses of pain, and/or pronounced local adverse events were also observed.

Accordingly, it is surprising that benzyl alcohol, which has a short duration of action, was found to reduce the pain due to a headache (such as a migraine) in a subject. In some embodiments, the subject experiences a complete reduction in pain associated with the headache. In some embodiments, the headache pain does not return for a period of 2-96, 2-90, 2-84, 2-78, 2-72, 2-60, 2-48, 2-36, 2-24, 2-12, 2-10, 2-8, 2-6, or 2-4 hours. In other embodiments, the headache pain does not return for 2, 3, 4, 5, 6, 7, 8, 9, 10, 11, 12, 13, 14, 15, 16, 17, 18, 19, 20, 21, 22, 23, 24, 30, 36, 42, 48, 54, 60, 66, or 72 hours. In some embodiments, the headache pain does not return for 1, 2, 3, 4, 5, 6, 7, 8, 9, 10, 11, 12, 13, or 14 days. In some embodiments, the headache pain does not return for 1, 2, 3, or 4 weeks. In some embodiments, the headache pain does not return for more than 1, 2, 3, or 4 weeks. In one embodiment, the headache is a migraine.

Tetracaine is unique in that it is both stable and highly protein bound compared to nearly all other local anesthetics. Because of its protein-bound nature and smaller molecular weight, tetracaine is better able to penetrate and adhere to the protein-covered membranes of nerve cells and is better able to penetrate the nerve so as to induce an anesthetic effect (especially when present in a pharmaceutical composition containing at least some of, e.g., surfactants, emulsifiers, solvents, pH modifiers, cell membrane solubilizers, and preservatives) when compared to other ester-based anesthetics such as cocaine, procaine, chloroprocaine and benzocaine. In addition, other ester-based local anesthetics are very toxic in small amounts and have also been shown to be unstable. Amide-based local anesthetics such as lidocaine, mepivacaine, bupivacaine, etidocaine, prilocaine, and ropivacaine, while protein bound, are not as effective as tetracaine (especially compared to pharmaceutical compositions of the present invention comprising benzyl alcohol and tetracaine) and produce significant systemic adverse drug reactions.

It has been found that administration of a composition comprising a combination of benzyl alcohol and tetracaine is more effective at reducing pain associated with headaches than compositions comprising benzyl alcohol alone. Without being bound by a particular theory, it is believed that the increase in efficacy is due to a synergistic effect between benzyl alcohol and tetracaine. For example, benzyl alcohol is known to act as a penetration enhancer which may facilitate access of the tetracaine and other ingredients that help molecules to the site of action.

In the context of the present invention, tetracaine may also reduce pain associated with headaches (e.g., migraines) via a non-anesthetic pathway. Specifically, production of nitric oxide in the nasopharynx and toncilar tissue is not uncommon. Nitric oxide is a known vasodilator and, thus, may play a role in headache pain. Tetracaine, which reduces nitric oxide production, may thus reduce pain associated with headaches by decreasing the amount of vasodilation of the circulation around the cranial nerves causing compression anesthesia on the nerve and some pain fibers.

Accordingly, the present invention generally provides intranasal pharmaceutical compositions comprising (i) benzyl alcohol (i.e., Table 1 Pharmaceutical Composition); and (ii) benzyl alcohol and tetracaine (i.e., Table 2 Pharmaceutical Composition). Such pharmaceutical compositions are useful for treating pain associated with headaches. In some embodiments, the headache is a primary headache such as a migraine, tension-type headache, cluster headache, or other headache (e.g., stabbing, cough, exertional, hypnic, or thunderclap headache). In some embodiments, the headache is a secondary headache such as one attributed to head and/or neck trauma, cranial and/or cervical vascular disorders, non-vascular intracranial disorders, substance use, withdrawal from substance use, infection, physical disorders or psychiatric disorders. In one embodiment, the headache is a migraine.

More specifically, the present invention provides a pharmaceutical composition for intranasal administration comprising: a) benzyl alcohol; and b) a pharmaceutically acceptable carrier. In other embodiments, the pharmaceutical composition comprises a) benzyl alcohol; b) a viscosity enhancing agent; and c) a pharmaceutically acceptable carrier. In some embodiments, the pharmaceutical composition further comprises a preservative. In some embodiments, the composition comprises about 0.6-1.2% (w/v) benzyl alcohol. In other embodiments, the composition comprises about 0.75-1.05% (w/v) benzyl alcohol. In a particular embodiment, the composition comprises about 0.9% (w/v) benzyl alcohol.

In another aspect, the invention provides a pharmaceutical composition for intranasal administration comprising: a) benzyl alcohol; b) tetracaine, or a pharmaceutically acceptable salt thereof; and c) a pharmaceutically acceptable carrier. In other embodiments, the pharmaceutical composition comprises a) benzyl alcohol; b) tetracaine, or a pharmaceutically acceptable salt thereof; c) a viscosity enhancing agent; and d) a pharmaceutically acceptable carrier. In some embodiments, the pharmaceutical composition further comprises a preservative. In some embodiments, the composition comprises about 0.6-1.2% (w/v) benzyl alcohol. In other embodiments, the composition comprises about 0.75-1.05% (w/v) benzyl alcohol. In a particular embodiment, the composition comprises about 0.9% (w/v) benzyl alcohol. In some embodiments, the composition comprises about 2-4% (w/v) tetracaine. In some embodiments, the composition comprises about 2.5-3.5% (w/v) tetracaine. In some embodiments, the composition comprises about 3% (w/v) tetracaine. In a particular embodiment, the composition comprises 0.9% (w/v) benzyl alcohol and 3% (w/v) tetracaine.

Headaches are generally believed to be caused by the constriction of peripheral arteries and the dilation of cerebral blood vessels. For example, it is hypothesized that vasoconstriction leads to a loss of cerebral oxygen in the blood, a loss which is then compensated for by vasodilation (i.e., rebound vasodilation). Nerve terminals in the trigeminal ophthalmic branch release vasodilatory and inflammatory chemicals (e.g., CGRP, substance P, neurokinin A). As discussed above, the release of these chemicals causes vasodilation and inflammation which, in turn, causes activation of the spinal trigeminal nucleus which processes pain. Accordingly, vasoconstrictors may not be suitable for inclusion in the pharmaceutical compositions of the present invention, especially if present at relatively high levels.

Without being bound by a particular theory, a lack of vasoconstriction may contribute to the efficacy of the pharmaceutical compositions of the present invention. For example, it is well known that circulation retrograde flow exists in the cranial vasculature. Thus, a lack of vasoconstriction—i.e., an environment which allows for blood flow—may allow circulation retrograde flow to carry the pharmaceutical compositions (or at least components active in relieving pain) to sites of action.

However, relatively low amounts of vasoconstrictors (e.g., less than an amount typically seen in over-the-counter drugs) may be suitable for use in the pharmaceutical compositions of the present invention. Thus, in some embodiments, the pharmaceutical composition of this invention comprises a vasoconstrictor such as, but not limited to, indirect $\alpha_1$-adrenergic agonists such as phenylephrine; calcium channel blockers; magnesium channel blockers; meperidine; imidazole drugs such as oxymetazoline and xylometazoline; $\alpha_2$-adrenergic agonists such as guanfacine; imidazoline ($I_1$) ligands; direct $\alpha_2$-adrenergic agonists such as clonidine; substance P blockers/reducers such as capsaicin; l-menthol; icilin; and glutamate receptor inhibitors; or pharmaceutically acceptable salts thereof. In some embodiments, the vasoconstrictor includes but is not limited to oxymetazoline, xylometazoline, guafacine, clonidine, phenylephrine, meperidine, capsaicin; l-menthol; icilin and pharmaceutically acceptable salts thereof. In some embodiments, the vasoconstrictor is oxymetazoline, or a pharmaceutically acceptable salt thereof. In other embodiments, the oxymetazoline is an oxymetazoline HCl salt.

The concentration of vasoconstrictor used in the pharmaceutical composition of the instant invention will depend on the specific vasoconstrictor. Typically, the amount used should be enough to garner a benefit from the compound's inclusion, but not enough to cause a vasoconstricting effect. For example, if oxymetazoline.HCl is used, enough of the compound should be administered for it to exhibit its anesthetic affect. Oxymetazoline affects G-protein coupled receptors and, in turn, $K^+$, $Na^+$, $Mg^{2+}$, NMDA, and $Ca^{2+}$ channels present in nerve cells. In particular, oxymetazoline enhances $K^+$, $Na^+$ and $Ca^{2+}$ permeability such that the nerve is no longer polarized and, thus, is unable to fire and transmit pain impulses. Yet, the amount of oxymetazoline used is preferably below the amount needed to trigger a vasoconstricting effect. Suitable ranges of concentrations include but are not limited to about 0.001-0.05%, 0.001-0.04%, 0.001-0.03%, 0.001-0.02%, and 0.001-0.01% (w/v). Suitable amounts of oxymetazoline include, but are not limited to, 0.001-0.5 mg, 0.001-0.45 mg, 0.001-0.40 mg, 0.001-0.35 mg, 0.001-0.30 mg, 0.001-0.29 mg, 0.001-0.28 mg, 0.001-0.27 mg, 0.001-0.26 mg, 0.001-0.25 mg, 0.001-0.24 mg, 0.001-0.23 mg, 0.001-0.22 mg, 0.001-0.21 mg, 0.001-0.20 mg, 0.001-0.19 mg, 0.001-0.18 mg, 0.001-0.17 mg, 0.001-0.16 mg, 0.001-0.15 mg, 0.001-0.14 mg, 0.001-0.13 mg, 0.001-0.12 mg, 0.001-0.11 mg, 0.001-0.10 mg, 0.001-0.09 mg, 0.001-0.08 mg, 0.001-0.07 mg, 0.001-0.06 mg, 0.001-0.05 mg, 0.001-0.04 mg, 0.001-0.03 mg, 0.001-0.02 mg, and 0.001-0.01 mg.

In some embodiments, the pharmaceutical composition of this invention further comprises a preservative (i.e., in addition to benzyl alcohol which is itself a preservative). Examples of preservatives include, but are not limited to sugar alcohols (e.g., sorbitol and mannitol), chlorobutanol, benzalkonium chloride, alcohols (e.g., ethanol, isopropanol, chlorobutanol, cresol, chlorocresol, and phenol) and benzalkonium chloride (BAK).

The concentration of preservative used in the pharmaceutical composition of the instant invention will depend on the specific preservative. Typical ranges of concentrations of preservatives are about 0.1-5% (w/v). In some embodiments, the composition comprises about 0.5-2.0% (w/v). In other embodiments, the composition comprises about 0.9% (w/v) (e.g., benzyl alcohol).

The benzyl alcohol, the tetracaine (when present), and other agents used in the compositions of the present invention may be dispersed in an appropriate carrier in order to control the dosage, absorption rate and other desired properties. Pharmaceutically acceptable carriers useful in the present invention include but are not limited to aqueous carriers, gel carriers, emulsifiers, surfactants, time release vehicles, nanoparticles, microspheres, intra- and para-cellular transport chemicals, polymers, liposomes, nanoparticles, and chitin. Examples of aqueous carriers include, but are not limited to, water, buffers (e.g., phosphate buffer, citrate buffer), sugar alcohols, alcohols such as ethanol, or any other solvent that is biologically compatible with the target tissue.

Saline is not an appropriate carrier for use with the compositions of the present invention. Specifically, it has been discovered that the compositions of the present invention are unstable in saline as exhibited by the formation of a precipitate. Without being bound by a particular theory, it is believed that the precipitate occurs as a result of an interaction between tetracaine.HCl and the chlorine ion present in saline solution via the common ion effect.

The pH of the pharmaceutical composition of the present invention is typically adjusted to be compatible with the pH of the tissue to which it is being administered (e.g., the nasal cavity). Typically, the composition has a pH of about 4.0-6.5. In some embodiments, the composition has a pH of about 5.5-6.5. In further embodiments, the pharmaceutical composition has a pH of about 6.0 to about 6.5. In some embodiments, the composition has a pH which is approximately 2 units lower than the pKa of tetracaine (which is approximately 8.4). The skilled artisan will appreciate that higher or lower pHs than those recited may be required and would readily know how to adjust the pH accordingly.

In addition, the anesthetic effect of a compound at a particular pH may be related to its pKa. For compounds which may exist in an unionized or ionized form, the unionized form is typically more effective as an anesthetic due to its ability to penetrate across membranes and bind to intracellular local anesthetic receptors. Accordingly, local anesthetics with pKas close to physiological pH are associated with more rapid onset of action due to a useful ratio of ionized to unionized forms. Notably, 1-2% of tetracaine molecules are unionized at pH 7.4; the pH of the nasal cavity varies from 4-6.5.

In some embodiments, the pharmaceutical composition of this invention further comprises a viscosity enhancing agent. Examples of viscosity enhancing agents include, but are not limited to methylcellulose, hydroxyethylcellulose, hydroxypropylmethylcellulose and smart hydrogel. In some embodiments, the viscosity enhancing agent is hydroxyethylcellulose.

Viscosity enhancing agents aid in controlling the mobility of the pharmaceutical composition before, during, and after application of the pharmaceutical composition to a target body part, tissue or organ. For example, viscosity enhancing agents aid in controlling the amount of pharmaceutical composition that either drips out of the nostrils or into the throat of the subject by reducing the mobility of the applied pharmaceutical composition. Viscosity enhancing agents also increase the amount of time the pharmaceutical composition is in contact with the vasculature (e.g., nasal vasculature) which helps to increase the uptake efficiency of the pharmaceutical composition to the vasculature. In addition, viscosity enhancing agents further dilute moieties present in the nasal passage that degrade esters (e.g., esterase) and can be mildly cilio-inhibitory.

The concentration of viscosity enhancing agent used in the pharmaceutical composition of the instant invention will depend on the specific viscosity enhancing agent. Typical ranges of viscosity enhancing agents, include 0.01 to 5% (w/v). In some embodiments, the pharmaceutical composition comprises about 0.01-1.0% (w/v). In other embodiments, the composition comprises about 0.05% (w/v) (e.g., hydroxyethylcellulose). The inventors have observed that compositions comprising high amounts of viscosity enhancing agents (e.g., hydroxyethylcellulose) result in clogging of the spray apparatus (e.g., the BD Accuspray™ device).

In one embodiment, the pharmaceutical composition of the present invention comprises the following components: benzyl alcohol, anhydrous citric acid (for pH control), sodium hydroxide (for pH adjustment), hydrochloric acid (for pH control), hydroxyethylcellulose, and purified water.

In another embodiment, the pharmaceutical composition of the present invention comprises the following components: benzyl alcohol, tetracaine HCl, anhydrous citric acid (for pH control), sodium hydroxide (for pH adjustment), hydrochloric acid (for pH control), hydroxyethylcellulose, and purified water.

In a particular embodiment, the pharmaceutical composition of the present invention is the Table 1 Pharmaceutical Composition. In another embodiment, the pharmaceutical composition of the present invention is the Table 2 Pharmaceutical Composition.

In one embodiment, the Table 1 and/or Table 2 Pharmaceutical Composition has a pH of between about 4.0-6.5. In another embodiment the Table 1 and/or Table 2 Pharmaceutical Composition has a pH of between about 5.5-6.5. In another embodiment the Table 1 and/or Table 2 Pharmaceutical Composition has a pH of about 6.0 to about 6.5.

The pharmaceutical compositions of the present invention may be administered in several forms. Examples of suitable pharmaceutical compositions include, but are not limited to, solutions, sprays, suspensions, oils, and emulsions.

In other embodiments, the pharmaceutical compositions optionally comprise pharmaceutically acceptable excipients. Examples of pharmaceutically acceptable excipients include, but are not limited to, preservatives, surfactants, stabilizing agents, emulsifiers, antibacterial agents, buffering agents and viscosity modifying agents. Specific examples of such excipients are discussed above.

Examples of emulsifiers include, but are not limited to, acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine and xanthan gum.

Methods of Treating Headaches

It has been discovered that the pharmaceutical compositions of the present invention are useful for treating headaches. In particular, the pharmaceutical compositions of the present invention are useful for reducing or eliminating the pain associated with headaches. The headaches may be either primary or secondary headaches. In some embodiments, the headache is a primary headache such as a migraine, tension-type headache, cluster headache, or other headache (e.g., stabbing, cough, exertional, hypnic, or thunderclap headache). In some embodiments, the headache is a secondary headache such as one attributed to head and/or neck trauma, cranial and/or cervical vascular disorders, non-vascular intracranial disorders, substance use, withdrawal from substance use, infection, physical disorders or psychiatric disorders. In one embodiment, the headache is a migraine.

Figure 1:
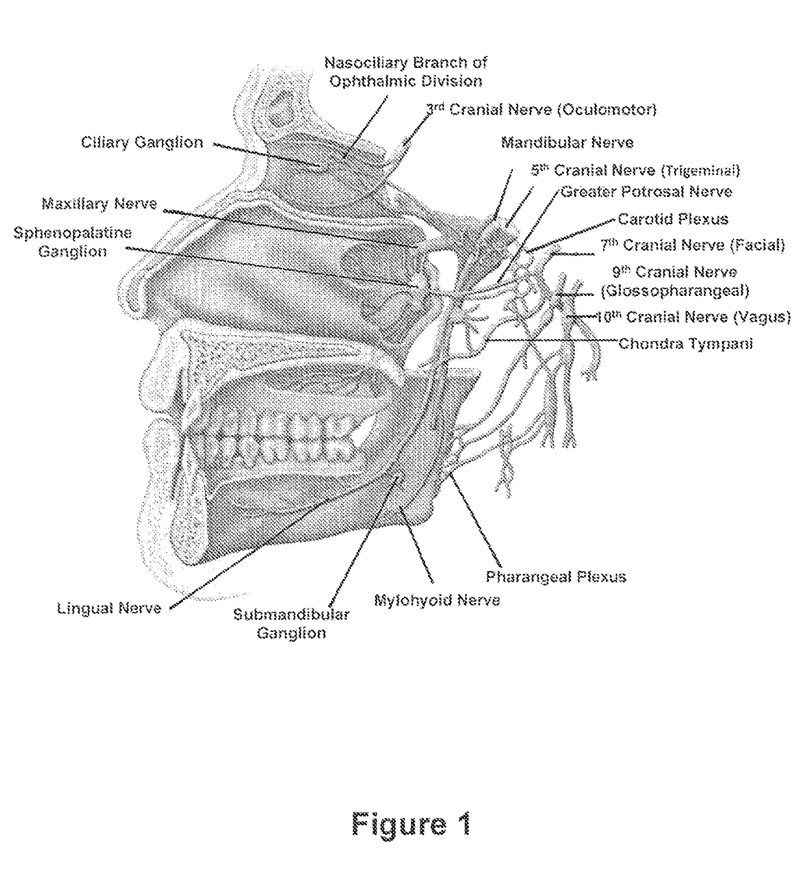
Figure 2:
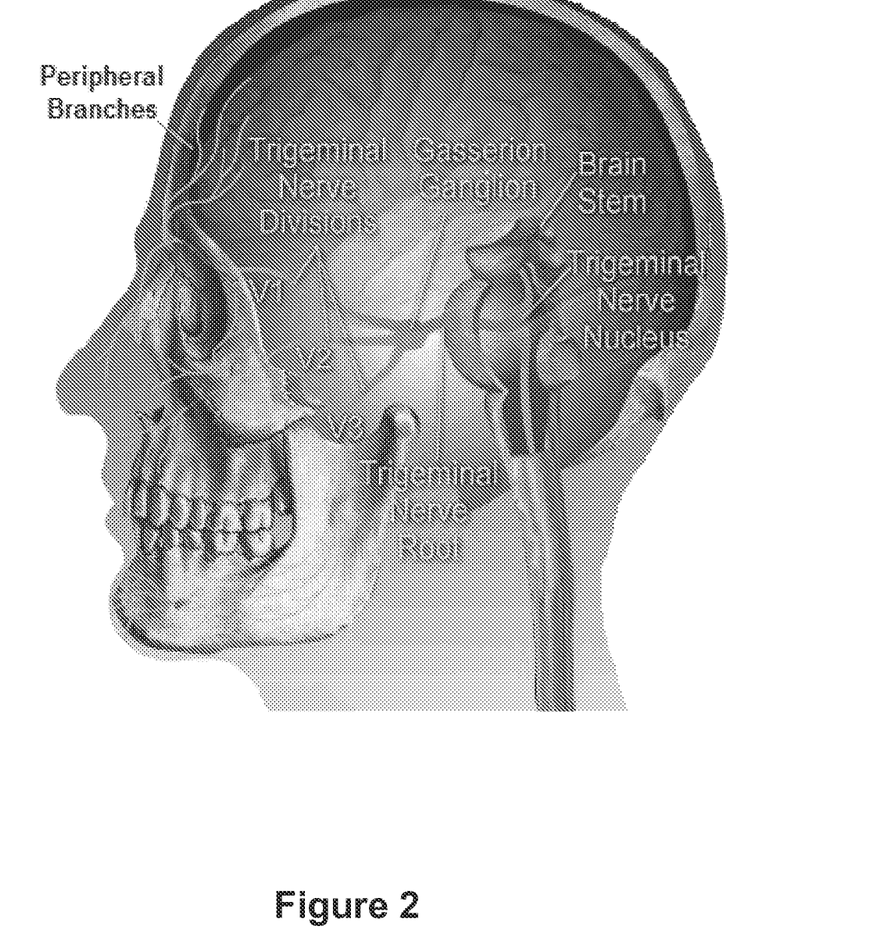
FIG. 2 illustrates a cross-sectional side view of a human cranium, specifically illustrating the anatomy of the trigeminal nerve.
Figure 3:
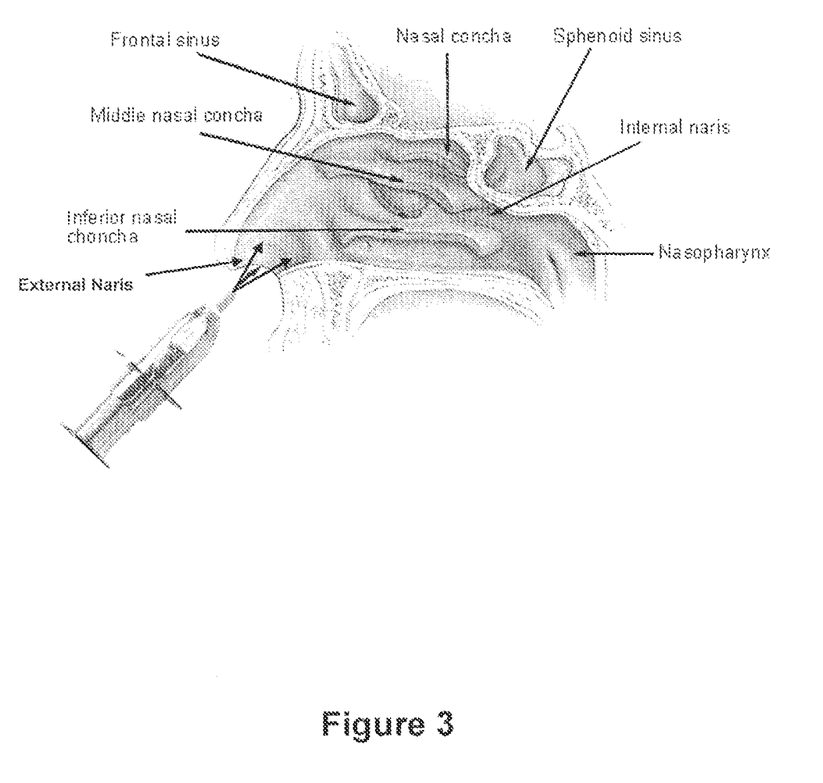

The nerves of the cranium are like branches of a tree that extend through the nasal cavity, nasopharynx, and tonsils branching down to various structures within the head. Although the exact "anatomy" of a headache (such as a migraine) is not known, the pain associated with headaches is generally attributed to the trigeminal pathway (i.e., cranial nerve 5); other associated cranial nerves such as cranial nerves 1, 3, 7, 9, and 12; secondary nerve branches such as the auriculotemporal nerve (branch of the mandibular nerve); and spinal nerves C-2, and C-3. See FIG. 1 for details.

When administered, lymphoepithelial tissues are exposed to the pharmaceutical composition. The pharmaceutical composition is typically administered to the nasopharynx, the superior soft palate, and/or the tonsillar area. In particular, the pharmaceutical composition may be applied to the Waldeyer's tonsillar ring and/or the fossa of Rosenmuller. Specifically, the pharmaceutical composition of the present invention is administered into the rear of the nasal cavity, affecting the base, or "trunk," of the nerve pathways. This targets the branches that transmit nerve impulses within the cranium, including the specific pathways (discussed above) carrying pain impulses associated with headaches.

Migraine headaches are typically caused by temporary problems that transmit pain through the above discussed structures. For example, pain associated with the oculomotor nerve is probably due to a spasm of the surrounding blood vessels. Pain sensation may result from stretching the dura, which is innervated by sensory nerves from the three divisions of the trigeminal or $5^{th}$ cranial nerve above the tentorium cerebelli and sensory branches from the second cervical nerve below its surface. Tugging on the venous sinuses or stretching the dura at the base of the brain can cause intense pain that is recognized as headaches. Almost any type of stretching stimulus to the blood vessels of the dura can also cause cephalagia.

The pharmaceutical compositions of the present invention enable molecular transport within the cranial tissues by one or more of the following mechanisms: diffusion, osmosis, vesicular transport, circulatory transport, intracellular transport, extracellular transport, axoplasmic transport to the above mentioned structures. With a wide and diverse penetration, these pharmaceutical compositions allow structures to be affected that would normally be inaccessible to conventional delivery of a pharmaceutical composition to areas of the nasal cavity and/or nasal sinuses.

Thus, the present invention provides a method of treating a subject suffering from a headache with the pharmaceutical composition of the present invention in accordance with the methods described above. In some embodiments, the headache is a primary headache such as a migraine, tension-type headache, cluster headache, or other headache (e.g., stabbing, cough, exertional, hypnic, or thunderclap headache). In some embodiments, the headache is a secondary headache such as one attributed to head and/or neck trauma, cranial and/or cervical vascular disorders, non-vascular intracranial disorders, substance use, withdrawal from substance use, infection, physical disorders or psychiatric disorders. In one embodiment, the headache is a migraine. In some embodiments, the subject will experience a reduction in pain associated with the headache within 1-30, 1-25, or 1-20 minutes of treatment. In some embodiments, the subject will experience a reduction in pain associated with the headache within 1-15 or 1-10 minutes of treatment. In some embodiments, the subject will experience a reduction in pain associated with the headache within 1, 2, 3, 4, 5, 6, 7, 8, 9, 10, 11, 12, 13, 14, or 15 minutes of treatment. In some embodiments, the subject will experience a reduction in pain associated with the headache within 1, 2, 3, 4 or 5 minutes of treatment.

In other embodiments, the present invention provides a method of treating a subject suffering from a headache with the pharmaceutical composition of the present invention in accordance with the methods described above, wherein the subject experiences a partial reduction in pain associated with the headache. In some embodiments, the headache is a primary headache such as a migraine, tension-type headache, cluster headache, or other headache (e.g., stabbing, cough, exertional, hypnic, or thunderclap headache). In some embodiments, the headache is a secondary headache such as one attributed to head and/or neck trauma, cranial and/or cervical vascular disorders, non-vascular intracranial disorders, substance use, withdrawal from substance use, infection, physical disorders or psychiatric disorders. In one embodiment, the headache is a migraine. In other embodiments, the subject experiences at least a 5, 10, 15, 20, 25, 30, 35, 40, 45, 50, 55, 60, 65, 70, 75, 80, 85, 90, or 95% reduction in pain associated with the headache. In other embodiments, the subject experiences a 25, 50, or 75% reduction in pain associated with the headache In some embodiments, the subject experiences a complete reduction in pain associated with the headache. In some embodiments, the headache pain does not return for a period of 2-96, 2-90, 2-84, 2-78, 2-72, 2-60, 2-48, 2-36, 2-24, 2-12, 2-10, 2-8, 2-6, or 2-4 hours. In other embodiments, the headache pain does not return for 2, 3, 4, 5, 6, 7, 8, 9, 10, 11, 12, 13, 14, 15, 16, 17, 18, 19, 20, 21, 22, 23, 24, 30, 36, 42, 48, 54, 60, 66, or 72 hours. In one embodiment, the headache is a migraine.

Any delivery device may be used to apply the pharmaceutical composition to the nasal cavity. Examples of suitable delivery devices include, but are not limited to squeeze bottles, pneumatically pressurized devices, pump sprayers, positive pressure nebulizers and the like. In some embodiments, the device used is pre-filled with a pharmaceutical composition of the present invention.

Methods of the present invention for reducing or eliminating the pain associated with headaches (including migraines) comprise delivering a pharmaceutical composition of the present invention into the nasal cavity, wherein at least a portion of the pharmaceutical composition is absorbed by nasal tissue located in the nasopharynx, the superior soft palate, and/or the tonsillar area. In some embodiments, the method comprises delivering a pharmaceutical composition of the present invention wherein at least a portion of the pharmaceutical composition is absorbed by the Waldeyer's tonsillar ring and/or the fossa of Rosenmuller. When administered according to this method, lymphoepithelial tissues are exposed to the pharmaceutical composition. In accordance with this method, at least a portion of one or more of the $1^{st}$, $3^{rd}$, $5^{th}$, $7^{th}$, $9^{th}$, $10^{th}$, and $12^{th}$ cranial nerves (associated with the headache pain) are affected. In some embodiments, administration of the pharmaceutical composition does not produce facial numbness of the eye, surface of the nose, cheeks or lips. In some embodiments, the pharmaceutical composition is delivered by nebulization or spraying.

When administering the pharmaceutical compositions of the present invention into the nasal cavity of the subject, at least a portion of the pharmaceutical composition is absorbed by nasal tissue located at the rear of the nasal cavity in the vicinity of the nasopharynx, tonsillar tissue, sphenopalatine ganglion and, consequently, the maxillary nerve (and/or structures that communicate with the maxillary nerve), thereby affecting at least a portion of the nerves and pain fibers associated with the headache pain. The maxillary nerve as used herein refers to region of the nasal cavity where the posterior, middle and anterior superior alveolar nerves collect. In some embodiments, the pharmaceutical composition is delivered into the nasal sinuses and/or rear of the nasal cavity of the subject. In some embodiments, the pharmaceutical composition is delivered to the nasal sinuses such as the maxillary sinus. In other embodiments, the pharmaceutical composition is delivered to the anterior dental plexus, extensions of the middle superior nerve, the posterior superior alveolar nerve, the nociceptors of the facial and buccal nerve, and/or the sphenopalatine (pterygopalatine) ganglion. In some embodiments, the pharmaceutical composition is also delivered to parts of the trigeminal ganglion. After the impulses pass through the maxillary nerve and the main trunk of the trigeminal nerve, they are transmitted to the mid brain for processing and recognition. In other embodiments, the delivered spray is a stream or a plume.

Any delivery device may be used in the methods of the present invention. Examples of delivery devices suitable for intranasal administration include, but are not limited to squeeze bottles, syringes, pneumatically pressurized devices, pump sprayers, positive pressure nebulizers and the like. In some embodiments, the device used is pre-filled with a pharmaceutical composition of the present invention. In another embodiment, the device used is a BD Accuspray™ device.

In some embodiments, the method comprises spraying the intranasal pharmaceutical composition of the invention 1-5 times into each of the nostrils of the subject. In other embodiments, the method comprises spraying the pharmaceutical composition of the invention 3 times into each of the nostrils of the subject. In other embodiments, the method comprises spraying the pharmaceutical composition of the invention 2 times into each of the nostrils of the subject. In other embodiments, the method comprises spraying the pharmaceutical composition of the invention 1 time into each of the nostrils of the subject. In yet other embodiments, the method comprises spraying the pharmaceutical composition of the invention 1 time into the nostril located on the same side of the head as the predominant headache pain. In some embodiments, each of the sprays are administered within about 1-10 minutes, of each other. For example, spray #1 may be administered, followed by an interval of about 1-10 minutes, after which spray #2 is administered, followed by an interval of about 1-10 minutes after which spray #3 is administered, etc. In some embodiments, the interval between sprays is about 1-6 minutes. In some embodiments, the interval between sprays is about 2-6 minutes. In other embodiments, the interval between sprays is about 3-5 minutes. In yet other embodiments, the interval between sprays is about 4 minutes.

It has been found that the angle of spraying aids in targeting the pharmaceutical composition to the relevant portions of the nasal cavity described above. For example, where the pharmaceutical composition is delivered in 3 sprays, the following procedure may be used: For the first spray, the tip of the spray device can be positioned at an angle of about 35 to 45 degrees from the horizontal plane while the subject looks straight ahead. For the second spray, the tip of the spray device can be positioned at an angle of about −10 to +5 degrees from the horizontal plane while the subject looks straight ahead. The third spray can be delivered in the same fashion as the first spray. In some embodiments, the tip of the spray device can be positioned at an angle of about 42 degrees from the horizontal plane for the first and third sprays, and can be positioned at an angle of about zero degrees for the second spray. In other embodiments, the tip of the spray device is positioned approximately 0-2 mm inside the nasal valve during sprayings.

In some embodiments, a known (e.g., metered) amount of benzyl alcohol is delivered into the nasal cavity of the subject. In other embodiments, the known (e.g., metered) amount of benzyl alcohol is delivered into the nasal sinuses and/or rear of the nasal cavity of the subject. Typically, the amount of benzyl alcohol delivered to the nasal sinuses and/or rear of the nasal cavity of the subject is about 5.4 mg. In some embodiments, about 4.5, 3.6, 2.7, 1.8, or 0.9 mg of benzyl alcohol is delivered into the nasal sinuses and/or rear of the nasal cavity of the subject. In some embodiments, the composition comprises about 0.6-1.2% (w/v) benzyl alcohol. In some embodiments, the composition comprises about 0.75-1.05% (w/v) benzyl alcohol. In other embodiments, the composition comprises about 0.8-1.0% (w/v) benzyl alcohol. In yet other embodiments, a composition comprising about 0.85-0.95% (w/v) benzyl alcohol is used. In a particular embodiment, the composition comprises about 0.9% (w/v) tetracaine.

In some embodiments, a known (e.g., metered) amount of benzyl alcohol and tetracaine are delivered into the nasal cavity of the subject. In other embodiments, the known (e.g., metered) amount of benzyl alcohol and tetracaine are delivered into the nasal sinuses and/or rear of the nasal cavity of the subject. Typically, the amount of tetracaine delivered to the nasal sinuses and/or rear of the nasal cavity of the subject is about 12-50 mg of tetracaine. In some embodiments, about 15-24 mg of tetracaine is delivered into the nasal sinuses and/or rear of the nasal cavity of the subject. In some embodiments, about 15-20 mg of tetracaine is delivered into the nasal sinuses and/or rear of the nasal cavity of the subject. In some embodiments, the composition comprises about 2.0-5.0% (w/v) tetracaine. In some embodiments, the composition comprises about 2.25-4.75% (w/v) tetracaine. In other embodiments, the composition comprises about 2.5-4.0% (w/v) tetracaine. In yet other embodiments, a composition comprising about 2.5-3.5% (w/v) tetracaine is used. In a particular embodiment, the composition comprises about 3% (w/v) tetracaine.

Accordingly, in embodiments wherein benzyl alcohol and tetracaine are delivered into the nasal cavity of the subject, the amount of benzyl alcohol and tetracaine delivered to the nasal sinuses and/or rear of the nasal cavity of the subject may be about 5.4 mg of benzyl alcohol and about 18 mg of tetracaine. In some embodiments, about 3.6 mg of benzyl alcohol and about 12 mg of tetracaine is delivered into the nasal sinuses and/or rear of the nasal cavity of the subject. In some embodiments, about 1.8 mg of benzyl alcohol and about 6 mg of tetracaine is delivered into the nasal sinuses and/or rear of the nasal cavity of the subject. In some embodiments, the composition comprises about 0.6-1.2% (w/v) benzyl alcohol and about 2.0-5.0% (w/v) tetracaine. In some embodiments, the composition comprises about 0.75-1.05% (w/v) benzyl alcohol and about 2.25-4.75% (w/v) tetracaine. In other embodiments, the composition comprises about 0.8-1.0% (w/v) benzyl alcohol and about 2.5-4.0% (w/v) tetracaine. In yet other embodiments, a composition comprising about 0.85-0.95% (w/v) benzyl alcohol and about 2.5-3.5% (w/v) tetracaine is used. In a particular embodiment, the composition comprises about 0.90% (w/v) benzyl alcohol and about 3% (w/v) tetracaine.

In some embodiments, the particle size of the pharmaceutical composition delivered to the nasal sinuses and/or rear of the nasal cavity is about 5-50 microns. In other embodiments, the particle size of the pharmaceutical composition is about 10-20 microns. In some embodiments, the pharmaceutical composition is delivered in a manner such that at least 50% of the particles are at least about 10 microns or larger. In other embodiments, the pharmaceutical composition is delivered in a manner such that at least 65% of the particles are at least about 10 microns or larger. In other embodiments, the pharmaceutical composition is delivered in a manner such that at least 85% of the particles are at least about 10 microns or larger. In yet other embodiments, the pharmaceutical composition is delivered in a manner such that at least 90% of the particles are at least about 10 microns or larger. In further embodiments, the pharmaceutical composition is delivered in a manner such that at least 95% of the particles are at least about 10 microns or larger.

These and other embodiments of the invention may be further illustrated in the following non-limiting Examples.

EXAMPLES

Example 1: Abortive Treatment of Migraine Using Pharmaceutical Composition Comprising Benzyl Alcohol The Table 1 Pharmaceutical Composition was evaluated to determine if it was effective in aborting migraines in an otherwise healthy subject. The pharmaceutical composition was delivered in a BD Accuspray® mono-dose nasal spray device with backstop (BD Medical-Pharmaceutical Systems, Franklin Lakes, N.J.). Details for the subject treated are discussed below.

Administration

A total of 3×200 µl sprays of the Table 1 Pharmaceutical Composition were administered to the subject's right nostril as follows. In each administration, the Table 1 Pharmaceutical Composition was administered while at a refrigerator temperature of approximately 40° F. 200 µl of the Table 1 Pharmaceutical Composition were administered to the right nostril. After four minutes, an additional 200 µl were administered to the right nostril. After an additional four minutes, a final 200 µl were administered to the right nostril. During administration, the subject was lying down flat and the sprays were administered at a spray angle of approximately 30° with the subject's head tilted up at approximately a 30° angle.

Pain Rating

At the time of treatment, the subject was experiencing a migraine; treatment began 48 hours after the onset of migraine symptoms. The subject noted an approximately 20% reduction in migraine pain after 5 minutes and an approximately 70%-80% reduction in pain after 30 minutes.

Results

Administration of the Table 1 Pharmaceutical Composition resulted in rapid elimination of migraine associated pain. Accordingly, the Table 1 Pharmaceutical Composition is effective as a rapid and effective abortive treatment for migraines. Such a pharmaceutical composition may be used to reduce migraine pain symptoms alone or in combination with other therapies to treat migraine pain symptoms. Moreover, the Table 1 Pharmaceutical Composition may also be used prophylactically—i.e., as a means of preventing, e.g., recurring headaches.

Example 2: Abortive Treatment of Migraine Using Pharmaceutical Composition Comprising Benzyl Alcohol and Tetracaine The Table 2 Pharmaceutical Composition was evaluated to determine if it was effective in aborting migraines in otherwise healthy subjects. The pharmaceutical composition was delivered in a BD Accuspray® mono-dose nasal spray device with backstop (BD Medical-Pharmaceutical Systems, Franklin Lakes, N.J.). Details for subjects treated are discussed below.

Subject 1—Treatment #1

Administration

A total of 2×200 µl sprays of the Table 2 Pharmaceutical Composition were administered to each nostril of the subject as follows. In each administration, the Table 1 Pharmaceutical Composition was administered while at a refrigerator temperature of approximately 40° F. 200 µl of the Table 2 Pharmaceutical Composition were administered to each nostril. After four minutes, an additional 200 µl were administered to each nostril. During administration, the subject was lying down flat and the sprays were administered at a spray angle of approximately 30° with the subject's head tilted up at approximately a 30° angle.

Pain Rating

The subject was asked to rate the migraine pain on a scale of 0 to 10 (0 being no pain and 10 being extreme pain) before treatment and at certain time intervals after treatment. At the time of treatment, the subject was experiencing a migraine; treatment began 20 hours after the onset of migraine symptoms. The subject noted a reduction in migraine pain in as little as 100 seconds. The results are summarized below.

TABLE 3

| Time (minutes after treatment) | Pain Level | % Drop in Pain |
| --- | --- | --- |
| Before treatment | 9 | — |
| 5 | 2-3 | 75% |
| 13 | 1-2 | 85% |
| 20 | 0-1 | 95% |

TABLE 3-continued

| Time (minutes after treatment) | Pain Level | % Drop in Pain |
| --- | --- | --- |
| 45 | 0-1 | 95% |
| 90 | 0 | 100% (no headache) |

Results

Administration of the Table 2 Pharmaceutical Composition resulted in rapid and complete elimination of migraine associated pain. Accordingly, the Table 2 Pharmaceutical Composition represents a rapid and effective abortive treatment for migraines. Moreover, the Table 2 Pharmaceutical Composition may also be used prophylactically—i.e., as a means of preventing, e.g., recurring headaches.

Minor adverse reactions were observed including: numbing of the central incisors, upper lip, incisive papilla, and inside of the nose; stuffy nose; and general feeling of coldness.

The subject was pain-free for 1 week post-administration of the Table 2 Pharmaceutical Composition.

Subject 1—Treatment #2

Administration

A total of 3×200 µl sprays of the Table 2 Pharmaceutical Composition were administered were administered to the subject as follows. In each administration, the Table 1 Pharmaceutical Composition was administered while at a refrigerator temperature of approximately 40° F. 200 µl of the Table 2 Pharmaceutical Composition were administered to each nostril. After four minutes, an additional 200 µl were administered to each nostril. During administration, the subject was lying down flat and the sprays were administered at a spray angle of approximately 30° with the subject's head tilted up at approximately a 30° angle.

Pain Rating

At the time of treatment, the subject was experiencing a migraine; treatment began 54 hours after the onset of migraine symptoms. The subject noted an approximately 15% reduction in migraine pain 2 minutes after administration and a complete reduction in migraine pain (i.e., no migraine pain) after 20 minutes.

Results

Administration of the Table 2 Pharmaceutical Composition resulted in rapid and complete elimination of migraine associated pain. No return of migraine-relate pain was observed for 2 weeks. Accordingly, the Table 2 Pharmaceutical Composition represents a rapid and effective abortive treatment for migraines.

Subject 2—Treatment #3

Administration

A total of 3×200 µl sprays of the Table 2 Pharmaceutical Composition were administered to the subject's right nostril as follows. In each administration, the Table 2 Pharmaceutical Composition was administered while at a refrigerator temperature of approximately 40° F. 200 µl of the Table 2 Pharmaceutical Composition were administered to the right nostril. After four minutes, an additional 200 µl were administered to the right nostril. After an additional four minutes, a final 200 µl were administered to the right nostril. During administration, the subject was lying down flat and the sprays were administered at a spray angle of approximately 30° with the subject's head tilted up at approximately a 30° angle.

Pain Rating

At the time of treatment, the subject was experiencing a migraine; treatment began 3 days after the onset of migraine symptoms. The subject noted an approximately 15% reduction in migraine pain 2 minutes after administration and a complete reduction in migraine pain (i.e., no migraine pain) after 30 minutes.

Results

Administration of the Table 2 Pharmaceutical Composition resulted in rapid and complete elimination of migraine associated pain. No return of migraine-relate pain was observed for 2 weeks. Accordingly, the Table 2 Pharmaceutical Composition represents a rapid and effective abortive treatment for migraines.

What is claimed is:

1. A method for reducing or eliminating pain associated with a headache in a subject comprising selectively delivering intranasally to the subject a pharmaceutical composition, wherein said composition comprises:
   a) benzyl alcohol; and
   b) a pharmaceutically acceptable carrier,
wherein benzyl alcohol is the sole active agent in the pharmaceutical composition for reducing or eliminating pain associated with a headache in the subject.

2. The method according to claim 1, wherein at least a portion of the pharmaceutical composition is absorbed by nasal tissue located at the rear of the nasal cavity in the vicinity of the fossa of Rosenmuller, nasopharynx, tonsillar tissues, or the Waldeyer's tonsillar ring.

3. The method according to claim 1, wherein the subject experiences a reduction in pain associated with the headache within 1-20, 20-25, or 25-30 minutes of treatment.

4. The method according to claim 1, wherein the subject experiences a 25, 50, or 75% reduction in pain associated with the headache.

5. The method according to claim 1, wherein the subject experiences a complete reduction in pain associated with the headache.

6. The method according to claim 1, wherein said pharmaceutical composition is delivered by nebulization or spraying.

7. The method according to claim 6, wherein said delivered spray is a stream or a plume.

8. The method according to claim 7, wherein the method comprises spraying said pharmaceutical composition 1-5 times into each of the nostrils of said subject.

9. The method according to claim 1, wherein about 5.4 mg of benzyl alcohol is delivered intranasally to said subject.

10. The method according to claim 1, wherein about 1.8 mg of benzyl alcohol is delivered intranasally to said subject.

11. The method according to claim 1, wherein said headache is a migraine.

12. The method according to claim 1, wherein said composition comprises about 0.6-1.2% (w/v) benzyl alcohol.

13. A method for reducing or eliminating pain associated with a headache in a subject comprising selectively delivering intranasally to the subject a pharmaceutical composition, wherein said pharmaceutical composition consists of benzyl alcohol, citric acid, sodium hydroxide, hydrochloric acid, hydroxyethylcellulose, and water.

* * * * *